United States Patent
Vardanega

(10) Patent No.: US 8,870,935 B2
(45) Date of Patent: *Oct. 28, 2014

(54) INLET OPENING DEVICE FOR INFLATING A WARMING BLANKET

(75) Inventor: Michael Vardanega, Livermore, CA (US)

(73) Assignee: Covidien LP, Mansfield, MA (US)

(*) Notice: Subject to any disclaimer, the term of this patent is extended or adjusted under 35 U.S.C. 154(b) by 909 days.

This patent is subject to a terminal disclaimer.

(21) Appl. No.: 13/020,668

(22) Filed: Feb. 3, 2011

(65) Prior Publication Data

US 2011/0121221 A1   May 26, 2011

Related U.S. Application Data

(62) Division of application No. 11/528,217, filed on Sep. 27, 2006, now Pat. No. 7,901,443.

(51) Int. Cl.
*A61F 7/00* (2006.01)
*A61F 7/08* (2006.01)

(52) U.S. Cl.
CPC ......... *A61F 7/0097* (2013.01); *A61F 2007/006* (2013.01); *A61F 2007/0001* (2013.01)
USPC ............................ 607/107; 251/336; 251/337

(58) Field of Classification Search
CPC .... A61F 7/0097; A61F 7/08; A61F 2007/006
USPC .................. 607/107; 251/336, 337
See application file for complete search history.

(56) References Cited

U.S. PATENT DOCUMENTS

| | | | |
|---|---|---|---|
| 2,941,907 A | 6/1960 | Tousignant et al. | |
| 3,236,370 A | 2/1966 | Pereny et al. | |
| 3,410,266 A | 11/1968 | Krzewinski et al. | |
| 3,667,458 A | 6/1972 | Krebs | |
| 3,741,206 A | 6/1973 | Binard et al. | |
| 3,750,664 A | 8/1973 | Collins | |
| 3,835,851 A | 9/1974 | Villari | |
| 3,916,887 A | 11/1975 | Kelly | |
| 4,024,862 A | 5/1977 | Collins | |
| 4,089,331 A | 5/1978 | Hartigan et al. | |
| 4,334,529 A | 6/1982 | Wirth | |
| 4,807,644 A | 2/1989 | Sandhaus | |
| 4,867,230 A | 9/1989 | Voss | |
| 4,957,120 A | 9/1990 | Grier-Idris | |
| 5,125,238 A * | 6/1992 | Ragan et al. ................ | 62/259.3 |
| 5,165,400 A * | 11/1992 | Berke .......................... | 607/104 |
| 5,265,599 A * | 11/1993 | Stephenson et al. ......... | 607/104 |
| 5,443,488 A | 8/1995 | Namanye et al. | |
| 5,545,194 A * | 8/1996 | Augustine .................... | 607/104 |
| 5,697,963 A | 12/1997 | Augustine | |
| 5,728,145 A * | 3/1998 | Phlipot et al. ................ | 607/104 |
| 5,735,890 A | 4/1998 | Kappel et al. | |
| 5,817,147 A | 10/1998 | Wolf | |

(Continued)

Primary Examiner — Linda Dvorak
Assistant Examiner — Kaitlyn Smith
(74) Attorney, Agent, or Firm — Fletcher Yoder PC

(57) ABSTRACT

A warming blanket is provided that includes a first sheet and a second sheet sealed at least along a common edge. An air inlet is provided on the warming blanket where the first sheet and the second sheet are not sealed. An inlet opening device is attached to the inlet opening. The inlet opening device separates the first sheet from the second sheet at the inlet opening in the absence of an opposing force. Methods of forming and using the warming blanket are also provided.

20 Claims, 3 Drawing Sheets

(56) References Cited

U.S. PATENT DOCUMENTS

| | | | |
|---|---|---|---|
| 5,890,243 A | 4/1999 | Dickerhoff | |
| 5,997,572 A | 12/1999 | Arnold et al. | |
| 6,112,348 A | 9/2000 | Dickerhoff | |
| 6,167,885 B1 | 1/2001 | Hanssen | |
| 6,168,612 B1 | 1/2001 | Augustine et al. | |
| 6,176,870 B1 | 1/2001 | Augustine | |
| 6,203,567 B1 | 3/2001 | Augustine | |
| 6,800,087 B2 * | 10/2004 | Papay et al. | 607/104 |
| 6,994,720 B2 | 2/2006 | Gammons | |
| 7,096,870 B2 | 8/2006 | Lamprich et al. | |
| 7,108,713 B1 | 9/2006 | Augustine | |
| 7,172,616 B2 | 2/2007 | Scheussler et al. | |
| 7,409,953 B2 | 8/2008 | Griesbach, III | |
| 8,002,940 B2 * | 8/2011 | Pierre et al. | 156/292 |
| 2003/0023292 A1 * | 1/2003 | Gammons et al. | 607/109 |
| 2003/0135251 A1 | 7/2003 | Scheussler et al. | |
| 2006/0052851 A1 | 3/2006 | Anderson et al. | |
| 2006/0271134 A1 * | 11/2006 | Frey | 607/104 |
| 2007/0093884 A1 | 4/2007 | Anderson et al. | |
| 2008/0077207 A1 | 3/2008 | Vardanega | |
| 2008/0077209 A1 | 3/2008 | Vardanega | |
| 2011/0162659 A1 * | 7/2011 | Augustine | 128/849 |
| 2013/0041438 A1 * | 2/2013 | Loushin | 607/107 |
| 2013/0231723 A1 * | 9/2013 | Van Oudenallen et al. | 607/107 |

* cited by examiner

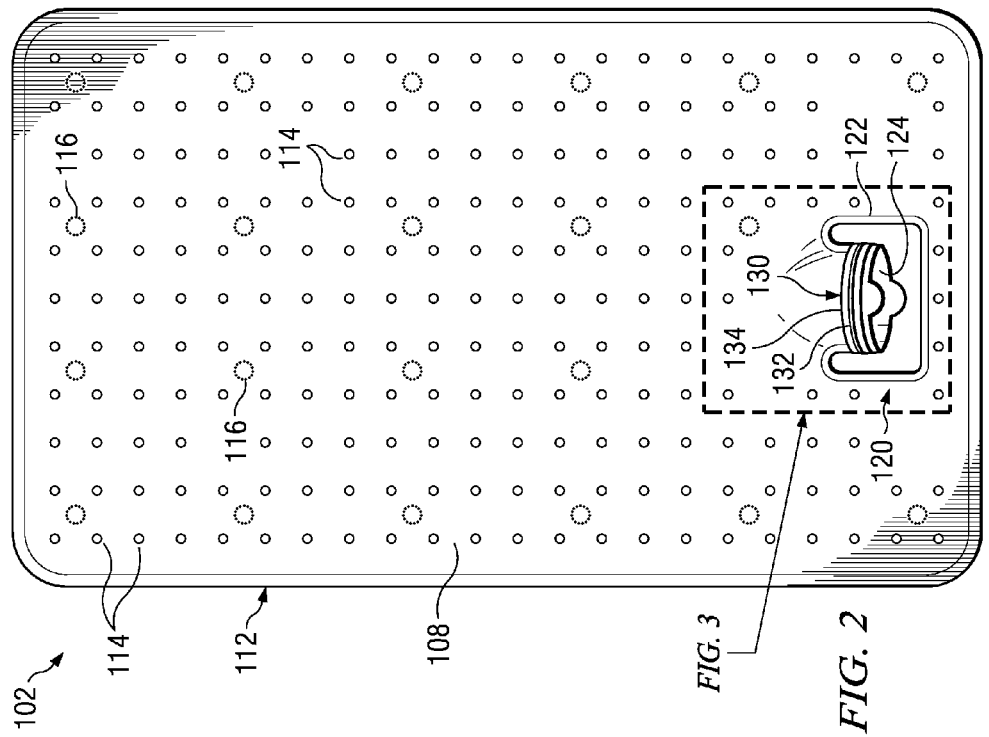
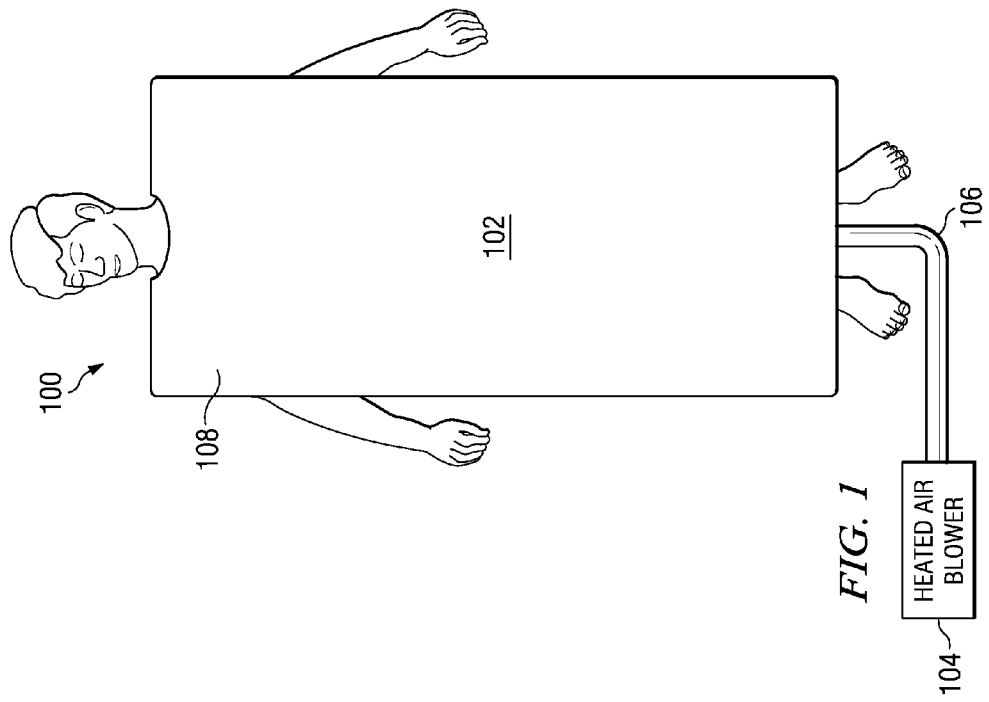

INLET OPENING DEVICE FOR INFLATING A WARMING BLANKET

CROSS-REFERENCE TO RELATED APPLICATIONS

This application is a divisional of U.S. patent application Ser. No. 11/528,217, entitled, Method and Apparatus for Inflating a Warming Blanket, filed on Sep. 27, 2006, which is incorporated by reference herein in its entirety.

BACKGROUND OF THE INVENTION

1. Field of the Invention

The present disclosure is generally related to materials and procedures for maintaining patient temperature.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A variety of medical environments are commonly maintained at temperatures well below body temperature to slow microbial growth, to counter the heat generated by medical lighting or equipment, or for various other reasons. For example, operating room temperatures of 65° F. (20° C.) and below are not uncommon. At such temperatures, it may be difficult to maintain the body temperature of the patient over time, such as over the course of a diagnostic, therapeutic, or surgical procedure.

To maintain patient temperature, a convective air warming blanket may be employed in the medical environment. Such a convective air warming blanket typically consists of two die cut sheets of material that are attached (such as by radio-frequency (RF) or ultra-sonic techniques) along their edges and at numerous internal weld locations. The internal welds limit the loft, i.e., height or thickness, of the warming blanket when inflated.

After the sheets forming the warming blanket are attached, the warming blanket may be die cut into the warming blanket's final shape. This die cut process, in which the sheets are cut simultaneously using a single die, results in their being little or no structural differentiation between the two sheets, making it difficult to separate the two sheets, particularly in contexts where gloves are worn or where personnel are occupied with other tasks. As a result, techniques for inflating the warming blanket that involve inserting a warm air blowing mechanism between the sheets may be difficult to perform, in turn making the inflation of the warming blanket a difficult process.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a warming blanket. The warming blanket includes a first sheet and a second sheet sealed at least along a common edge such that the first sheet and the second sheet define an internal volume when separated. An air inlet region is defined by a cutout of the first sheet and the second sheet. The air inlet region is generally sealed along the edges of the first sheet and the second sheet except along an inlet opening. An inlet opening device is attached to the inlet opening. The inlet opening device separates the first sheet from the second sheet at the inlet opening in the absence of an opposing force.

There is also provided a method of forming a warming blanket. The method includes the act of sealing a first sheet and a second sheet at least along a common edge. The edges of an air inlet region defined by a cutout of the first sheet and second sheet are sealed except along an inlet opening of the air inlet region. An inlet opening device is attached to the inlet opening such that the inlet opening device separates the first sheet from the second sheet at the inlet opening in the absence of an opposing force.

There is also provided a method of connecting a warming blanket. The method includes the act of removing a constraining force from about an inlet opening of a warming blanket such that an inlet opening device attached to the inlet opening separates a first sheet from a second sheet at the inlet opening.

There is further provided a warming assembly. The warming assembly includes a warming blanket. The warming blanket includes an inlet opening device attached to an inlet opening. The inlet opening device separates a first sheet from a second sheet of the warming blanket at the inlet opening. The assembly also includes a heated air blower and a hose configured to connect the heated air blower and the inlet opening.

There is also provided an inlet opening device. The inlet opening device includes a substrate configured to be attached to a first sheet and a second sheet of an inlet opening of a warming blanket. The inlet opening device also includes a tensioning member attached to the substrate such that the tensioning member deforms the substrate in the absence of an opposing force.

BRIEF DESCRIPTION OF THE DRAWINGS

Some embodiments of the disclosure may be understood by referring, in part, to the following description and the accompanying drawings, in which like reference numbers refer to the same or like parts and wherein:

FIG. 1 depicts a warming blanket assembly in accordance with one aspect of the present technique;

FIG. 2 depicts one embodiment of a warming blanket in accordance with one aspect of the present technique;

DETAILED DESCRIPTION OF SPECIFIC EMBODIMENTS

Figure 3:
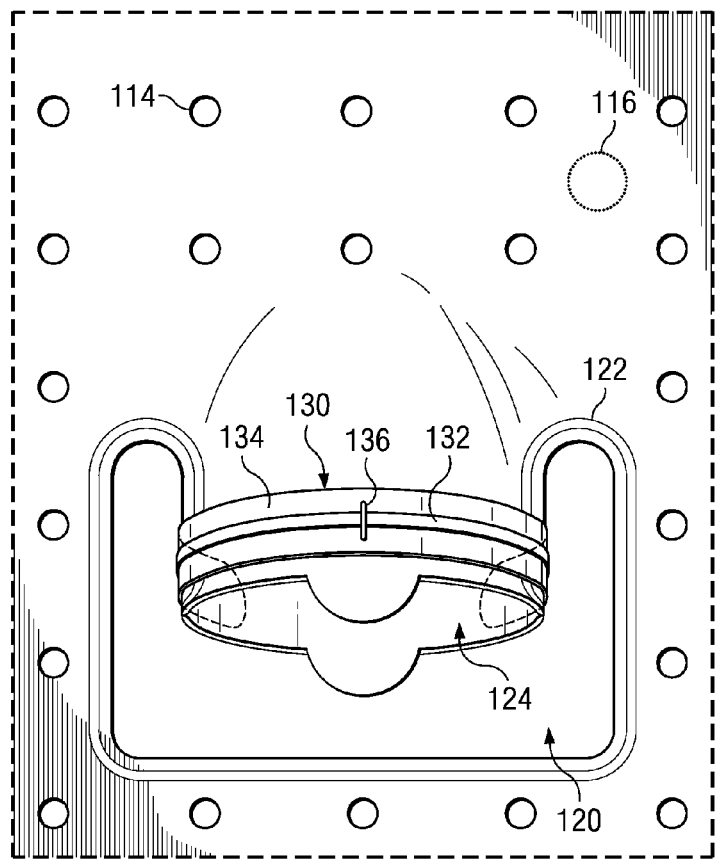
FIG. 3 depicts an air inlet region of the warming blanket of FIG. 2, in accordance with one aspect of the present technique.

In some embodiments of the present technique, a warming blanket is employed that allows easy connection to a warm air blower. For example, in one embodiment, the warming blanket is provided with a device to facilitate the separation of the sheets forming the warming blanket at an air inlet of the warming blanket. In one embodiment, the device includes a strip of cardboard or other suitable material that is configured with a tensioning member, such as an elastic strap. In such an embodiment, when the device is attached to an air inlet of the warming blanket, the tension provided by the device causes the respective sheets forming the warming blanket to separate, thereby creating an opening in which a warm air delivery mechanism, such as a hose, can be inserted.

Referring now to FIG. 1, an embodiment of a warming assembly 100 is depicted. In the depicted embodiment, warming assembly 100 includes a warming blanket 102, a heated air blower 104, and hosing 106 connecting the warming blanket 102 and heated air blower 104. As suggested by its name, heated air blower 104 produces and expels heated air. A commercially distributed device suitable for use as heated air blower 104 is the WarmTouch® 5200/5300 series of warming units from the Nellcor division of Tyco Healthcare. For example, in an embodiment of warming assembly 100 that implements heated air blower 104 with a WarmTouch® 5300 warming unit, heated air may be provided to warming blanket 102 at predefined temperatures of 32° C., 38° C., 43°, or 45° C. In the depicted embodiment, heated air from heated air blower 104 is provided to warming blanket 102 through the hosing 106 via an entry port or other opening in warming blanket 102 as described in greater detail below.

Referring now to FIG. 2, a top view of one embodiment of the warming blanket 102 is depicted. In one embodiment, the warming blanket 102 includes a first sheet 108 bonded or otherwise attached to a second sheet 110 (see FIGS. 3 and 5). In one implementation of the warming blanket 102, the first sheet 108 is a polyester material while the second sheet 110 is a polypropylene. In an embodiment of the warming blanket 102 suitable for use in a surgical environment, the warming blanket 102 is approximately 150 to 220 centimeters long approximately 90 to 150 centimeters wide.

In certain embodiments, the warming blanket 102 may be constructed using a die that cuts the first sheet 108 and the second sheet 110 simultaneously so that the shape of the first sheet 108 coincides with the shape of the second sheet 110. In such an embodiment, an airtight seal 112 may be formed along the perimeter of the first and second sheets 108 and 110 such that heated air entering the warming blanket 102 cannot exit along the perimeter of the warming blanket 102. Instead, the heated air blown into the warming blanket 102 exits via air openings 114 that are disposed (such as in an array) on at least one surface of the warming blanket 102.

In some embodiments, the perimeter seal 112 is formed by applying localized heat to the first and second sheets 108 and 110 when the sheets are aligned and in contact with one another. In some of these embodiments, the localized heat causes the fusion of the materials forming the first and second sheets 108 and 110. In other embodiments, the localized heat causes the fusion of a coating or film (such as a polyethylene coating or film) applied to one or both of the first and second sheets 108 and 110. In such an embodiment, the coating or film, when heated, fuses with the material forming the other sheet or with a like coating or film disposed on the other sheet. Such an embodiment may be useful where the compositions of the first and second sheet are not easily fusible themselves but are each fusible with the film or coating composition, such as polyethylene.

Furthermore, some embodiments of the warming blanket 102 may include an array of weld points 116. The weld points 116 may be formed in the same manner as the perimeter seal 112, such as by the localized application of heat when the surfaces of the first and second sheets are in contact. As with the perimeter seal 112, the materials forming the first and second sheets 108 and 110 may fuse directly or a film or coating on the sheets, such as the aforementioned polyethylene coating, may be fused to form the weld points 116. The weld points 116 serve to control the loft or range of separation of the first and second sheets 108 and 110 when the warming blanket 102 is inflated.

As depicted in FIG. 2, the warming blanket 102 includes an air inlet region 120. The air inlet region 120 is generally sealed along the edges by an inlet seal 122 that circumscribes most but not the entire air inlet region 120. The portion of the air inlet region 120 that is not sealed is the inlet opening 124. For example, referring to the embodiment depicted in FIG. 3, inlet seal 122 terminates at the edges of the inlet opening 124, allowing the first and second sheet 108 and 110 of the warming blanket 102 to be separated at the inlet opening 124. Separation of the first and second sheet 108 and 110 at the inlet opening 124 results in the inlet opening 124 being opened such that a hose (such as hose 106 of FIG. 1) or nozzle may be inserted into the inlet opening 124.

FIG. 3 also depicts an embodiment of an inlet opening device 130 that acts to open the inlet opening 124 in the absence of an opposing force. In the depicted embodiment, the inlet opening device 130 partially surrounds the inlet opening 124 and is attached to the inlet opening 124 along the length of the opening device 130 or at specific locations. The embodiment of inlet opening device 130 depicted in FIG. 3 circumscribes a majority, but not all, of the inlet opening 124 formed by the unsealed edges of first and second sheets 108 and 110. In other implementations, the inlet opening device 130 may fully circumscribe inlet opening 124.

Figure 4:
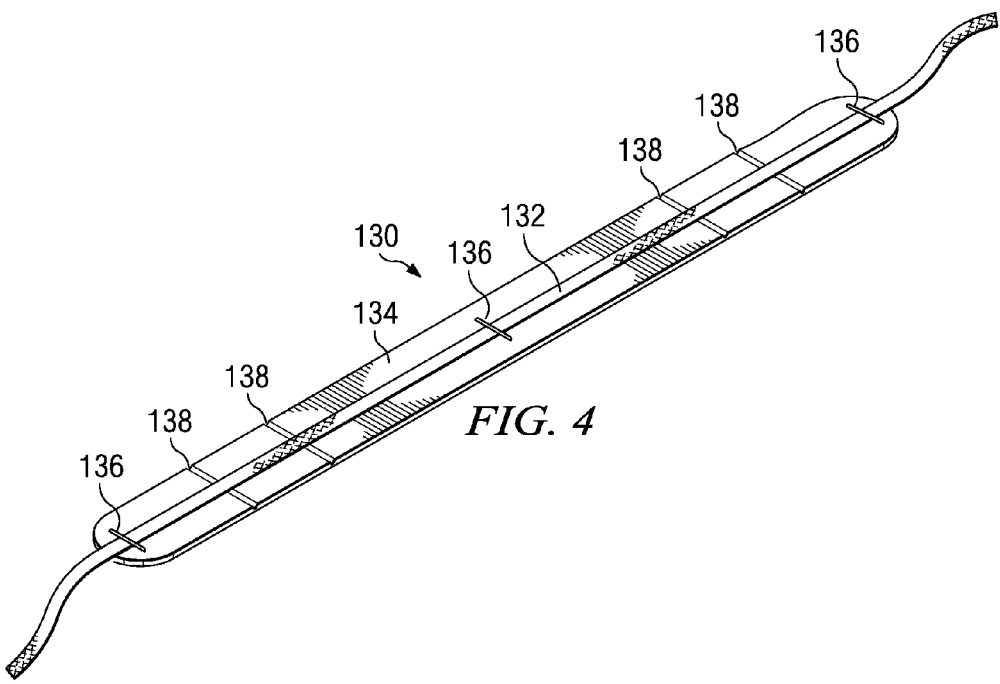
FIG. 4 depicts a port opening device suitable for use with the warming blanket of FIG. 2, in accordance with one aspect of the present technique.

In one embodiment, the inlet opening device 130 (depicted in greater detail in FIG. 4) includes a tensioning member 132, such as an elastic band or other bias providing component, attached to a substrate 134, such as a strip of rigid or semi-rigid paper, cardboard, metal and/or plastic material. In one embodiment, the tensioning member 132 is a one-eighth inch thick elastic band. In the depicted embodiment, the tensioning member 132 is fastened to the substrate by mechanical fasteners, such as the depicted staples 136. In other embodiments, the tensioning member 132 may be attached to the substrate 134 by other means, such as adhesives, or by other chemical and/or mechanical attachment mechanisms. When so attached, the tensioning member 132 applies a biasing force to the substrate 134 that acts to bend or deform the substrate 134 in the absence of an opposing force. In one embodiment, substrate 134 is scored at predetermined fold locations 138 near its ends so that the bias provided by tensioning member 132 causes substrate 134 to fold where scored.

Figure 5:
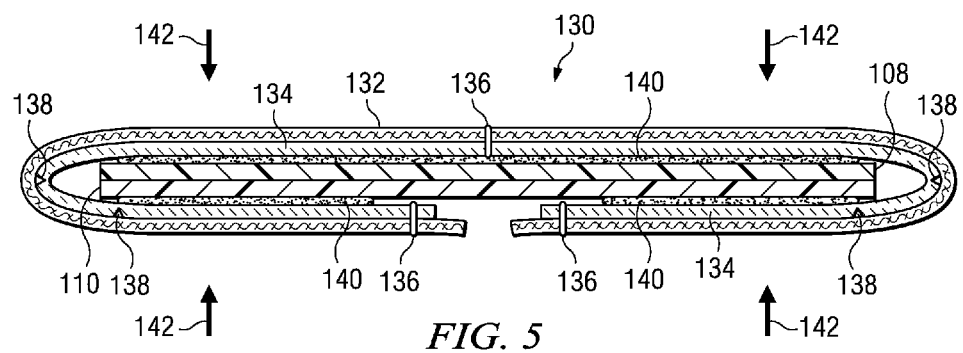
FIG. 5 depicts a cross-sectional view of the inlet opening and inlet opening device in a closed configuration, in accordance with one aspect of the present technique.
Figure 6:
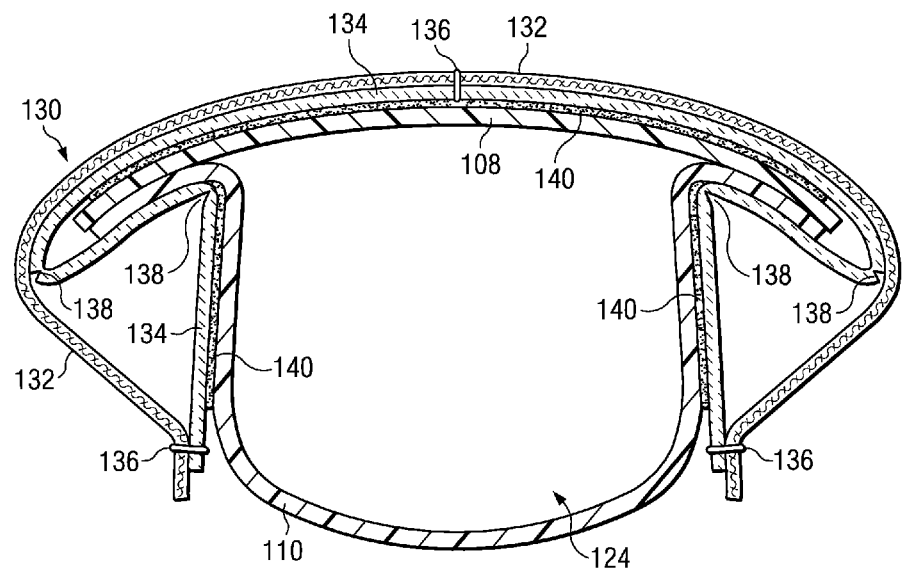
FIG. 6 depicts a cross-sectional view of the inlet opening and inlet opening device in an open configuration, in accordance with one aspect of the present technique.

Referring to FIGS. 5 and 6, for example, one embodiment of inlet opening device 130 includes four fold locations 140. In the depicted embodiment, the inlet opening device 130 is attached to the first and second sheets 108 and 110 at the inlet opening 124. The inlet opening device 130 may be attached to the inlet opening 124 using an adhesive 140 or glue or by other suitable attachment mechanisms. In the depicted implementation, the central portion of inlet opening device 130 is affixed to first sheet 108 while end portions of inlet opening device 130 are affixed to second sheet 110.

As depicted in FIG. 5, in the present of an opposing force, depicted as force arrows 142, the tensioning member 132 does not deform the substrate 134 of the inlet opening device 130 and, thus, does not cause the inlet opening 124 to open. In one embodiment, an opposing force of the type depicted by force arrows 142 may be provided by packaging within which the warming blanket 102 is packed or stored. Upon removal from the packaging, however, the opposing force is removed and, as depicted in FIG. 6, the tensioning member 132 can deform the substrate 134 of the inlet opening device 130, causing the inlet opening 124 to open without additional user intervention. For example, in the embodiment depicted in FIG. 6, unopposed tension in tensioning member 132 causes the substrate 134 of the inlet opening device 130 to bend or otherwise deform at fold locations 138. The attachment of substrate 134 to the first and second sheets 108 and 110 causes the first and second sheets 108 and 110 to separate at the inlet opening 124, thus opening the inlet opening 124. Thus, in one embodiment, by simply removing the warming blanket 102 from its packaging (or otherwise removing a constraining force), the inlet opening 124 is opened without further user intervention, allowing the user to insert hosing 106, or another warm air blowing mechanism, into the opened inlet opening 124.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An inlet opening device, comprising:
   a substrate configured to be attached to a first sheet and a second sheet of an inlet opening of a warming blanket; and
   a tensioning member attached to the substrate such that the tensioning member deforms the substrate in the absence of an opposing force.

2. The inlet opening device of claim 1, wherein the substrate comprises a rigid or semi-rigid material.

3. The inlet opening device of claim 1, wherein the substrate comprises at least one of a paper, cardboard, metal, or plastic composition.

4. The inlet opening device of claim 1, wherein the tensioning member comprises an elastic material.

5. The inlet opening device of claim 1, wherein the first sheet comprises a polypropylene sheet and the second sheet comprises polyester.

6. The inlet opening device of claim 1, wherein the substrate comprises one or more fold locations where the substrate is predisposed to bend when tension is applied to the substrate by the tensioning member.

7. The inlet opening device of claim 1, wherein the tensioning member automatically separates the first sheet from the second sheet unless held closed.

8. The inlet opening device of claim 1, wherein the inlet opening is configured to connect to a hose and a heated air blower.

9. The inlet opening device of claim 1, comprising a mechanical fastener, wherein the tensioning member is attached to the substrate by the mechanical fastener.

10. The inlet opening device of claim 1, wherein the tensioning member is attached to the substrate by an adhesive.

11. An inlet opening device, comprising:
    a substrate configured to be attached to a first sheet and a second sheet of an inlet opening of a warming blanket; and
    a biasing component attached to the substrate, wherein the biasing component biases the substrate to an open position.

12. The inlet opening device of claim 11, wherein the substrate comprises a rigid or semi-rigid material.

13. The inlet opening device of claim 11, wherein the substrate comprises at least one of a paper, cardboard, metal, or plastic composition.

14. The inlet opening device of claim 11, wherein the biasing component comprises an elastic material.

15. The inlet opening device of claim 14, wherein the biasing component comprises a one-eighth inch thick elastic band.

16. The inlet opening device of claim 11, wherein the substrate comprises one or more fold locations where the substrate is predisposed to bend when biased by the biasing component.

17. The inlet opening device of claim 11, wherein the biasing component separates the first sheet from the second sheet without user intervention unless force is applied to overcome the force biasing the inlet opening device to the open position.

18. The inlet opening device of claim 11, wherein the biasing component is attached to the substrate via staples.

19. The inlet opening device of claim 11, wherein a central portion of the substrate is attached to the first sheet of the inlet opening and an end portion of the substrate is attached to the second sheet of the inlet opening.

20. The inlet opening device of claim 11, wherein the substrate is attached to the inlet opening via adhesive.

* * * * *